United States Patent [19]

Alderete

[11] Patent Number: 5,679,551
[45] Date of Patent: Oct. 21, 1997

[54] **UNIQUE DOUBLE-STRANDED RNAS ASSOCIATED WITH THE *TRICHOMONAS VAGINALIS* VIRUS**

[75] Inventor: John F. Alderete, San Antonio, Tex.

[73] Assignee: Board of Regents, The University of Texas System, Austin, Tex.

[21] Appl. No.: 551,275

[22] Filed: Oct. 31, 1995

[51] Int. Cl.$^6$ .................................................. C12P 21/00
[52] U.S. Cl. ................. 435/70.1; 435/71.1; 435/258.1; 435/320.1; 536/23.1; 536/24.1; 536/243
[58] Field of Search ........................... 435/69.1, 172.1, 435/252.3, 320.1, 23, 57, 72, 70.1, 71.1, 243, 258.1; 536/23.1, 24.1, 24.3

[56] References Cited

PUBLICATIONS

Alderete et al., "Cloning and molecular characterization of two genes encoding adhesion proteins involved in *Trichomonas vaginalis* cytoadherence", *Molecular Microbiology*, 17(1):69–83, 1995.

Alderete, "*Trichomonas vaginalis* NYH286 Phenotypic Variation May Be Coordinated for a Repertoire of Trichomonad Surface Immunogens", *Infection and Immunity*, 55(9):1957–1962, 1987.

Alderete and Kasmala, "Monoclonal Antibody to a Major Glycoprotein Immunogen Mediates Differential Complement–Independent Lysis of *Trichomonas vaginalis*", *Infection and Immunity*, 53(3):697–699, 1986.

Alderete and Neale, "Relatedness of Structures of a Major Immunogen in *Trichomonas vaginalis* Isolates", *Infection and Immunity*, 57(6):1849–1853, 1989.

Alderete et al., "Phenotypes and Protein–Epitope Phenotypic Variation among Fresh Isolates of *Trichomonas vaginalis*", *Infection and Immunity*, 55(5):1037–1041, 1987.

Alderete et al., "Monoclonal Antibody to a Major Surface of Glycoprotein Immunogen Differentiates Isolates and subpopulations of *Trichomonas vaginalis*", *Infection and Immunity*, 52(1):70–75, 1986.

Alderete et al., "Phenotypic Variation and Diversity among *Trichomonas vaginalis* Isolates and Correlation of Phenotype with Trichomonal Virulence Determinants", *Infection and Immunity*, 53(2):285–293, 1986.

Alderete et al., "The vagina of women infected with *Trichomonas vaginalis* has numerous proteinases and antibody to trichmonad proteinases", *Genitourin Med*, 67:469–474, 1991.

Coombs and North, "An analysis of the proteinases of *Trichomonas vaginalis* by polyacrylamide gel electrophoresis", *Parasitology*, 86:1–6, 1983.

Dailey and Alderete, "The Phenotypically Variable Surface Protein of *Trichomonas vaginalis* Has a Single, Tandemly Repeated Immunodominant Epitope", *Infection and Immunology*, 59(6):2083–2088, 1991.

Khoshnan and Alderete, "Characterization of Double–Stranded RNA Satellites Associated with the *Trichomonas vaginalis* Virus", *Journal of Virology*, 69(11):6892–6897, 1995.

Khoshnan et al., "Unique Double–Stranded RNAs Associated with the *Trichomonas vaginalis* Virus Are Synthesized by Viral RNA–Dependent RNA Polymerase", *Journal of Virology*, 68(11):7108–7114, 1994.

Khoshnan and Alderete, "Multiple Double–Stranded RNA Segments Are Associated with Virus Particles Infecting *Trichomonas vaginalis*", *Journal of Virology*, 67(12):6950–6955, 1993.

Khoshnan and Alderete, "*Trichomonas vaginalis* with a Double–Stranded RNA Virus Has Upregulated Levels of Phenotypically Variable Immunogen mRNA", *Journal of Virology*, 68(6):4035–4038, 1994.

Lehker and Alderete, "Properties of *Trichomonas vaginalis* grown under chemostat controlled growth conditions", *Genitourin Med*, 66:193–199, 1990.

Neale and Alderete, "Analysis of the Proteinases of Representative *Trichomonas vaginalis* Isolates", *Infection and Immunity*, 58(1):157–162, 1990.

Provenzano and Alderete, "Analysis of Human Immunoglobin–Degrading Cysteine Proteinases of *Trichomonas vaginalis*", *Infection and Immunity*, 63(9):3388–3395, 1995.

Roditi et al., "Virus–like particles in *Eimeria nieschulzi* are associated with multiple RNA segments", *Molecular and Biochemical Parasitology*, 63:275–282, 1994.

Rodriguez–Cousino et al., "Molecular Cloning and Characterization of W Double–stranded RNA, a Linear Molecular Present in *Saccharomyces cerevisiae*", *The Journal of Biological Chemistry*, 266(19):12772–12778, 1991.

Tai et al., "The Divergence of *Trichomonas vaginalis* Virus RNAs among Various Isolates of *Trichomonas vaginalis*", *Experimental Parasitology*, 76:278–286, 1993.

Tipper and Schmitt, "Yeast dsRNA viruses: replication and killer phenotypes", *Molecular Microbiology*, 5(10):2331–2338, 1991.

Wang et al., "*Trichomonas vaginalis* Phenotypic Variation Occurs Only Among Trichomonads Infected With The Double–Stranded RNA Virus", *J. Exp. Med.*, 166:142–150, 1987.

Wang and Wang, "The double–stranded RNA in *Trichomonas vaginalis* may originate from virus–like particles", *Proc. Nat'l. Acad. Sci. USA*, 83:7956–7960, 1986.

Wang and Wang, "A Linear Double–stranded RNA in *Trichomonas vaginalis* *", *The Journal of Biological Chemistry*, 260(6):3697–3702, 1985.

Weeks et al., "LRV1 Viral Particles in *Leishmania guyanensis* Contain Double–Stranded or Single–Stranded RNA", *Journal of Virology*, 66(3):1389–1393, 1992.

(List continued on next page.)

*Primary Examiner*—James Ketter
*Assistant Examiner*—Wem Yucel
*Attorney, Agent, or Firm*—Arnold, White & Durkee

[57] ABSTRACT

Disclosed are nucleic acid sequences encoding satellite RNA's associated with the dsRNA virus of *Trichomonas vaginalis*. The use of the satellite molecules as vectors for the insertion of foreign genetic material into *Trichomonas vaginalis* protozoans infected with dsRNA virus is also disclosed.

21 Claims, No Drawings

OTHER PUBLICATIONS

Weeks et al., "Transcribing and replicating particles in a double–stranded RNA virus from Leishmania", *Molecular and Biochemical Parasitology*, 52:207–214, 1992.

White and Wang, "RNA dependent RNA polymerase activity associated with the double–stranded RNA virus of *Giardia lamblia*", *Nucleic Acids Research*, 18(3):553–559, 1990.

Widmer et al., "RNA Polymerase Activity Is Associated with Viral Particles Isolated from *Leishmania braziliensis* subsp. *guyanensis*", *Journal of Virology*, 64(8):3712–3715, 1990.

Tai et al., "Identification of a satellite double–stranded RNA in the parasitic protozoan *Trichomonas vaginalis* infected with *T. vaginalis* virus T1", Virol. 208: 189–196 Apr. 1995.

Tai et al., direct submission of Sequence accession No. U15991 to embl Oct. 1994.

UNIQUE DOUBLE-STRANDED RNAS ASSOCIATED WITH THE *TRICHOMONAS VAGINALIS* VIRUS

BACKGROUND OF THE INVENTION

1. Field of the Invention

The present invention relates generally to the field of protozoan flagellates, especially *Trichomonas vaginalis* and more particularly to double stranded RNA viruses that infect *T. vaginalis* and satellite sequences associated with the dsRNA virus.

2. Description of the Related Art

Flagellate protozoa can be found in the mouth, vagina, or intestine of almost all vertebrates, and it is common for an animal host to harbor more than one species. Humans may serve as host and reservoir to eight luminal flagellates but only two cause disease. Of these, *Giardia lamblia* inhabits the intestinal tract and *Trichomonas vaginalis* inhabits the vagina and genital tract (Plorde, 1984).

*Trichomonas vaginalis* causes trichomoniasis, a common sexually transmitted infection. It is estimated that 3 million women acquire this disease annually in the United States, and 25% of sexually active women are infected at any given time. Presumably, men are similarly involved, but data on this point are lacking. The clinical syndrome in women ranges from asymptomatic carriage to frank vaginitis. Men tend to have more asymptomatic disease but may develop urethritis. The likelihood of acquiring the disease correlates directly with the number of sexual contacts. Infection is rare in adult virgins, whereas rates as high as 70% are seen among prostitutes, sexual partners of infected patients, and individuals with other venereal disease.

Nonvenereal transmission is uncommon. Transfer of organisms on shared washcloths may explain, in part, the high frequency of infection seen among institutionalized women. Female neonates are occasionally noted to harbor *T. vaginalis*, presumably acquiring it during passage through the birth canal.

The diagnosis of trichomoniasis rests on the detection and morphologic identification of the organism in the genital tract. Identification is accomplished most easily by examining a wet mount preparation for the presence of motile organisms. Although highly specific when positive, wet mounts are often negative in asymptomatic or mildly symptomatic patients and in women who have douched in the previous 24 hr. Giemsa and Papanicolaou stained smears provide little additional help. Cultures of urogenital specimens may increase the number of detected cases. Unfortunately, this procedure is not generally available in clinical laboratories and requires several days to complete.

Some isolates of *Trichomonas vaginalis* are persistently infected with a double-stranded ribonucleic acid (dsRNA) virus called TW (Patterson, 1990; Wang and Wang, 1991). Recent investigations have revealed that TVV-infected trichomonads, including the original isolate from which TW was isolated (Wang, A. and C. C. Wang, 1986), contain at least 3 unique dsRNA segments (L, M and S) ranging from 4.8 to 4.3 kbp (Khoslman, A. and J. F. Alderete, 1993). All three segments were associated with the 33 nm isometric viral particles. TVV appears to lack an infectious cycle, and virus-minus isolates are resistant to infection by purified virus particles obtained from the cytoplasmic fraction of infected cultures (Khoshnan, A. and J. F. Alderete, 1993; Wang, A. and C. C. Wang, 1986).

In contrast to dsRNA viruses found in other protozoan pathogens (Patterson, 1990; Wang and Wang, 1991), in which no biological role has been established for the dsRNA, the presence of the dsRNA virus in *T. vaginalis* has been correlated with phenotypic variation with respect to surface versus cytoplasmic expression of a highly immunogenic protein called P270, (Alderete et al., 1987; Alderete et al., 1986; Wang et al., 1987).

Two types of *T vaginalis* isolates have been described with respect to surface expression and phenotypic variation of P270 (Alderete et al., 1986; Alderete et al., 1987; Alderete et al., 1986; Alderete, J. F., 1987). Type I isolates were homogenous populations of parasites that synthesized P270 but were unable to express the immunogen on the surface. Type II isolates, on the other hand, comprised a heterogenous population of trichomonads whereby some parasites had P270 on the surface (Alderete et al., 1986; Alderete et al., 1987; Alderete et al., 1986). Each subpopulation of Type II organisms, however, underwent a phenotypic variation between surface and cytoplasmic expression of P270 (Alderete, et al., 1986). Only Type II isolates were found to harbor TVV ($V^+$) (Wang et al., 1987), and interestingly, loss of TVV from Type II parasites resulted in a transition of trichomonads toward Type I ($V^-$) (Alderete et al., 1986; Wang et al., 1987).

The relationship between the presence of TVV and the phenotypic variation indicated that in virus-harboring parasites, transcription of the phenotypically varying P270 gene was up-regulated (Khoshnan and Alderete, 1994), resulting in elevated mounts of P270 and shows that the presence of virus influences expression of this and other trichomonad proteins, including cysteine proteinases (Provenzano and Alderete, 1995). Antibody to the repeated epitope of P270, in fact, is cytolytic in a complement-independent fashion (Alderete, J. F. and L. Kasmala, 1986) and is found in the sera of patients with trichomoniasis (Alderete et al., 1987). Also noteworthy was that during subcutaneous infection of mice with $V^+$ trichomonads, anti-P270 antibody was detected coincident with a shift of parasites from those with P270 on the surface to those without surface P270. The ability to alternate from surface expression to cytoplasmic expression of an immunogen may allow the parasite to evade the host antibody responses (Alderete et al., 1986; Alderete et al., 1987) and contribute to persistence of this pathogen at the site of infection.

Up to 70 percent of fresh clinical isolates have been found to harbor TVV (Khoshnan, A. and J. F. Alderete). It is possible that all isolates, in vivo, have TVV but some isolates lose the virus upon placement in a complex medium for in vitro cultivation (Diamond, L. S., 1968).

It is also noteworthy that virus-harboring trichomonads, which surface-express the immunogen P270, synthesize lower mounts of adhesins, i.e., surface proteins essential for binding of *T. vaginalis* to target cells (Arroyo et al., 1992). These same trichomonads are less adherent and correspondingly less cytotoxic to HeLa cells in vitro (Alderete et al., 1986).

That a dsRNA virus confers hypovirulence through modulation of virulence factor expression has precedence in the chestnut blight fungus, *Endothia parasitica* (Nuss, D. L., 1992). Furthermore, the presence of a dsRNA virus has been reported only in the pathogenic isolates of Phytomonas, although its association with disease induction remains unknown (Marche et al., 1993). These findings illustrate the extent to which a dsRNA virus infection of pathogens may influence virulence and, therefore, pathogenesis.

The molecular characterization of TVV, and its mechanism of replication is not understood. Other protozoan dsRNA viruses, like Giardia and Leishmania (LR1), contain an RNA-dependent RNA polymerase (RDRP) in the assembled particles, and RDRP is responsible for the transcription and replication of the viral genomes (Weeks et al., 1992; White, C. T. and C. C. Wang, 1990; Widmer et al., 1990). Further molecular cloning and nucleotide sequence analysis of cDNAs to the Leishmania and Giardia dsRNA viruses have confirmed the existence of this enzyme in the vital dsRNA genome (Smart et al., 1992; Wang et al., 1993).

The inability to infect virus-minus trichomonads has been a major impediment to understanding the biological properties of the virus, the virus-parasite relationship and the influence of the virus, if any, on expression of parasite- and/or viral-encoded virulence factors, apart from the phenotypic variation property (Alderete et al., 1986). Molecular characterization of these viral RNAs found within *T. vaginalis* and the establishment of conditions which will allow for infection of isolates without detectable virus and/or viral dsRNAs may eventually elucidate the relationship between the virus and virulence properties of this sexually transmitted protozoan.

Therefore there is a need for a vector capable of being shuttled into the *T. vaginalis* parasite such that the vector is able to carry foreign genetic material to be replicated and expressed in the protozoan. This vector will be a valuable aid to the clinical and medical research communities in the diagnosis and treatment of protozoan parasites.

SUMMARY OF THE INVENTION

The present invention seeks to fulfill these and other needs in the field by providing novel vectors capable of carrying foreign gene sequences into a protozoan host so that the vector and inserted nucleic acid sequences are replicated and expressed in the host. The present invention will thus allow the expression of a variety of genes, including but not limited to marker genes such as i.e. antibiotic markers, host genes containing mutations, antisense RNA molecules, genes under the control of inducible promoters, virulence genes of sexually transmitted diseases such as chlamydia, gonorrhea or HIV, and even attenuation genes that diminish virulence. For example, an organism expressing genes that diminish the virulence could be administered as whole organism vaccines.

In certain embodiments, the present invention may be described as an isolated nucleic acid segment consisting essentially of a sequence in accordance with SEQ ID NO: 1 or SEQ ID NO:3 or the complement of SEQ ID NO:1 or SEQ ID NO:3. As used herein, "consisting essentially of" is contemplated to mean that the claimed sequence primarily consists of the disclosed sequences. However, it is understood that there may be some sequence either 5' or 3' of the disclosed sequence that may result from a number of events, such as the use of particular cloning vectors, the occurrence of restriction enzyme sites in the region of the gene used for isolating the particular sequence, etc. In addition, the claimed sequence may contain one or a few base changes or small deletions or insertions within the sequence without changing the essential nature and function of the molecule. For example, an isolated (single) base change may occur once, twice or even three times in the entire sequence, or even once in 100 bases, once in 50 bases, once in 30 bases, or even once in 20 bases without changing the essential nature of the sequence. It is also understood that small deletions or insertions of one, two or even three bases may occur without changing the essential nature of the sequence and that all such minor changes would be included within the scope of the appended claims.

The complement of a DNA or RNA sequence is well known in the art and is based on the Watson-Crick pairing of nucleic acid polymers. The complement of a nucleic acid segment is generated by convening all "G" residues to "C" residues, all "C" residues to "G" residues, all "A" residues to "T" (in the case of DNA) or "U" (in the case of RNA) and all "T" or "U" residues to "A", and then reversing the 5' to 3' orientation of the generated sequence. As used herein therefore, the term "complement" defines a second strand of nucleic acid which will hybridize to a first strand of nucleic acid to form a duplex molecule in which all or most of the base pairs are matched as G:C, C:G, A:T/U or T/U:A.

The present invention may also be described in certain embodiments as a nucleic acid segment that is hybridizable to the nucleic acid segment of SEQ ID NO:1 or SEQ ID NO:3 under stringent conditions. Hybridizable is understood to mean capable of forming a double stranded molecule or a molecule with partial double stranded structure. Stringent conditions are those that allow hybridization between two nucleic acid sequences with some degree of homology, but precludes hybridization of random sequences. For example, hybridization at low temperature and/or high ionic strength is termed low stringency and hybridization at high temperature and/or low ionic strength is termed high stringency. Some examples of ranges that may be employed are for low stringency, from 0.15–0.9M NaCl at a temperature of 20°–50° C. might be employed, and for high stringency, from 0.02–0.15M NaCl at a temperature of 50°–70° C. might be employed. It is understood that the temperature and ionic strength of a desired stringency are applicable to particular probe lengths, to the length and base content of the sequences and to the presence of formamide or other solvents in the hybridization mixture and that these ranges are mentioned by way of example only.

The tendency for two complementary strands of nucleic acid in solution to anneal or hybridize by forming hydrogen bonds between their complementary bases, is critically dependent on the concentration of monovalent or divalent cations in the solution. Sodium ($Na^+$), has been the cation of choice for determining the effects of salt concentration on the stability of duplex nucleic acids. Above a threshold $Na^+$ concentration, two complementary single strands (either DNA or RNA) of nucleic acid will hydrogen bond through interaction of the bases in each strand, to form a double-stranded molecule of DNA, RNA, or even a DNA-RNA heteroduplex. Two hydrogen bonds are formed between paired A and T or A and U residues, while C–G base pairing results in the formation of three hydrogen bonds. The G–C base pair is therefore a stronger interaction than the A–U or A–T base pair. In general, hydrogen bonding (leading to duplex formation) does not occur between non-complementary bases. The ability of two single strands to form a stable double-stranded duplex depends on the sequence of bases in each strand being complementary to the other, such that when the strands are aligned in an antiparallel orientation, sequential juxtaposed bases are able to form hydrogen bonds. Although hydrogen bonding between any two complementary bases provides only a weak binding energy, the cumulative binding energy between many sequential paired bases provides sufficient attractive forces to hold the strands together in a stable duplex. Cations enhance the tendency for complementary strands to form hydrogen bonds, by masking the negative charges of the phosphate groups in the phosphodiester linkages which form the "backbone" of the nucleic acid strands. At low concentrations of positively charged ions, repulsive forces between negatively charged strands favor their single-stranded or denatured conformation; as cation concentration is raised, the negative charges are masked, complementary bases pair through hydrogen bonding, and a duplex nucleic acid molecule is formed.

Other parameters besides cation concentration affect the tendency of complementary strands to hybridize. Temperature is a critical variable; as the temperature of a solution of duplex nucleic acid molecules is raised, hydrogen bonds are broken first in A–U rich regions and finally in G–C rich regions, until above a critical temperature, the complementary strands come apart. The composition of the two strands, i.e., their % GC content, determines the critical temperature for duplex denaturation at a given ionic strength. As a corollary, the % GC also determines the threshold concentration of $Na^+$ needed to maintain duplex stability at a given temperature. Stability of duplex nucleic acid molecules in solution is also affected by the nature of the solvent. For example, duplexes are much less stable in formamide (which destabilizes hydrogen bonds) than in aqueous solution, a fact exploited by molecular biologists to achieve nucleic acid hybridization at lower temperatures than would otherwise be required.

Equations have been derived to relate duplex formation to the major variables of temperature, salt concentration, nucleic acid strand length and composition, and formamide concentration.

Eg:

1. $Tm=81.5-16.6(log[Na^+])+0.41(\%GC)-600/N$
   (Tm=temperature for duplex to half denature; N=chain length)
2. $Tm=81.5-16.6(log[Na^+]+0.41(\%GC)-0.63(\%formamide)-600/N$ One can thus predict whether complementary strands will hybridize under a given set of conditions.

It is understood in the art that a nucleic acid sequence will hybridize with a complementary nucleic acid sequence under high stringency conditions even though some mismatches may be present, particularly in complementary stretches of more than about 15 bases. Such closely matched, but not perfectly complementary sequences are also encompassed by the present invention. For example, differences may occur through genetic code degenerency, or by naturally occurring or man made mutations and such mismatched sequences would still be encompassed by the present claimed invention.

The nucleic acid sequences of the present invention may be RNA sequences, DNA sequences or even cDNA sequences. The present invention may also be defined as comprising a nucleic acid segment according to SEQ ID NO:1 or SEQ ID NO:3 and a polylinker region. The use of a polylinker region is well established in the art, and such a region is typically a segment of DNA or RNA that contains one, two or several restriction enzyme recognition sites. Thus, this region may be digested with a particular enzyme to create a compatible end to be used as a cloning site for the addition of a recombinant sequence to be fused to the sequences disclosed herein.

The present invention may also be described, in certain embodiments as an isolated nucleic acid segment comprising a sequence in accordance with SEQ ID NO:1 or SEQ ID NO:3 joined to a recombinant nucleic acid sequence and capable of being replicated by RNA dependent KNA polymerase (RDRP) activity in a protozoan host. The RDRP activity may be supplied by a virus such as a TVV infecting the host, or it may be encoded by a gene integrated into the host genome. However, the nucleic acid segment will contain a RDRP recognition site and other signal sequences necessary to replicate in the protozoan host, and preferably in a *Trichomonas vaginalis* host. The invention may also be described as a protozoan cell comprising a nucleic acid segment having a sequence in accordance with SEQ ID NO:1 or SEQ ID NO:3 joined with a recombinant sequence, and particularly preferred is a *Trichomonas vaginalis* cell.

An embodiment of the present invention is an RNA dependent RNA polymerase control sequence contained in SEQ ID NO:1 or SEQ ID NO:3. The control sequence may be a contiguous sequence, or it may be a combination of sequences embedded in the sequences of SEQ ID NO:1 or SEQ ID NO:3 that direct the replication of the molecule by the RNA dependent RNA polymerase activity provided by the TW. Such control sequences include, but are not limited to bases 682 through 688 of SEQ ID NO:1, bases 610 through 616 of SEQ ID NO:3, bases 562 through 572 of SEQ ID NO:1 and bases 500 through 510 of SEQ ID NO:3.

A further embodiment of the present invention may be described as method of expressing a recombinant gene in a TVV infected protozoan cell, and preferably in a Trichomonas cell and more preferably in a *Trichomonas vaginalis* cell. The method comprises the steps of preparing a nucleic acid molecule comprising a recombinant gene fused with or joined to a sequence in accordance with SEQ ID NO:1 or SEQ ID NO:3, transfecting the fused molecule into a TVV infected protozoan cell and culturing the cell under conditions appropriate for the expression of the recombinant gene. The recombinant gene may be fused to the 5' end, to the 3' end or even inserted into the interior of SEQ ID NO:1 or SEQ ID NO:3, or even to a portion of SEQ ID NO:1 or SEQ ID NO:3 that possesses the RDRP control regions as described herein. The recombinant gene may also comprise a promoter region, a ribosomal binding region, and a polyadenylation site and any other sequences necessary for expression in a host cell. The promoter may be a promoter normally associated with the gene to be expressed, or it may be a promoter selected for expression under any particular set of conditions and fused to the gene. The use of recombinant expression promoters is well known in the art, and all such promoters are understood to be within the scope of the appended claims. Particularly useful promoters would be those promoters derived from *T. vaginalis* genes, including but not limited to those conforming to the consensus *T. vaginalis* promoter, TCAYTWYTCATTA, SEQ ID NO:4, (Quon et al., 1994) and particularly embodied by the following promoter regions, each of which immediately precedes the ATG start site:

adhesin gene promoters (Alderete et al., 1995):
   TTTTTGATTAAAG, SEQ ID NO:5,
   TTTTTTTTGATTAAAG, SEQ ID NO:6,
   TTTTCAGATTAAAG, SEQ ID NO:7,
   TTTCAGATTAAAG, SEQ ID NO:8,
   TTTTCAGTTTCAGATTAG, SEQ ID NO:9;
ferrodoxin promoter (Alderete et al., 1995):
   TACTTCACTTCTCTTAGCGA, SEQ ID NO:10;
β-succinyl CoA synthetase promoter (Alderete et al., 1995):
   TTGATCACTTCACATTACA, SEQ ID NO:11;
α-succinyl CoA synthetase promoter (Alderete et al., 1995):
   TTGTTCACTTCACATTA, SEQ ID NO:12;
α-tubulin promoter (Alderete et al., 1995):
   AGTGTCACTCTTCATCA, SEQ ID NO:13;
70 kDa heat shock protein promoter (Alderete et al., 1995):
   CATCTCATTTTTTAATA, SEQ ID NO:14;
P-glycoprotein 1 promoter (Alderete et al., 1995):
   CAGACCATTAATCATTAGTG, SEQ ID NO:15; and
β-tubulin promoter (Quon et al., 1994):
   AATATCATTATTCAC, SEQ ID NO:16.

The DNA sequences disclosed herein will find utility as probes or primers in nucleic acid hybridization embodiments. As such, it is contemplated that oligonucleotide fragments corresponding to the sequences of SEQ ID NO:1 or SEQ ID NO:3 for stretches of from between about 15 to about 17, 20, or even about 30 nucleotides will find particular utility, with even longer sequences, e.g., 40, 50, 100 nucleotides, even up to full length, being more preferred for certain embodiments. The ability of such nucleic acid probes to specifically hybridize to satellite RNA sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having contiguous stretches of 15, 17, 20, 30, 40, 50, 75, 100, 150, 200, 300, 400, 500, 600 or 616 complementary to SEQ ID NO:1 or SEQ ID NO:3, or even contiguous stretches of 688 nucleotides complementary to SEQ ID NO:1 will also have utility as hybridization probes. These probes will be useful in a variety of hybridization embodiments, such as Southern and Northern blotting in connection with analyzing viral RNA or satellite RNA in various protozoan species. The total size of the fragment, as well as the size of the complementary stretches, will ultimately depend on the intended use or application of the particular nucleic acid segment. Smaller fragments will generally find use in hybridization embodiments, wherein the length of the complementary region may be varied, such as between about 17 and about 100 nucleotides, or even up to 686 according to the complementary sequences one wishes to detect.

The use of a hybridization probe of about 15 to 17 nucleotides in length allows the formation of a duplex molecule that is both stable and selective. Molecules having complementary sequences over stretches greater than 17 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 20 or 30 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (incorporated herein by reference) or by introducing selected sequences into recombinant vectors for recombinant production.

Accordingly, the nucleotide sequences of the invention may be used for their ability to selectively form duplex molecules with complementary stretches of protozoan viral genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g. , one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating the *Trichomonas vaginalis* dsRNA satellite virus sequences.

Preferred hybridization conditions and temperatures include a solution containing 50% (volume/volume) formamide, 5× Denhardt's solution, 6× SSC, 0.1% (weight/volume) SDS, and 100 µg/ml salmon sperm DNA, and 1 mM sodium pyrophosphate at 37° C. For nucleotide sequences longer than 50 nucleotides, preferred wash conditions include a solution containing 2× SSC/0.5% SDS at 25° C. for 30 min followed by one or more washes in a solution containing 0.2× SSC/0.5% SDS at 60° C. for 30 min per wash. For nucleotide sequences shorter than 50 nucleotides, preferred wash conditions include a solution containing 2× SSC/1% SDS at 25° C. for 30 min followed by one or more washes in a solution containing 2× SSC/1% SDS at 50° C. for 30 min.

Of course, for some applications, for example, where one desires to prepare mutants employing a mutant primer strand hybridized to an underlying template or where one seeks to isolate viral or satellite sequences from related species, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the circumstances based on the particular criteria required (depending, for example, on the G+C contents, type of target nucleic acid, source of nucleic acid, size of hybridization probe, etc.). Following washing of the hybridized surface to remove nonspecifically bound probe molecules, specific hybridization is detected, or even quantified, by means of the label.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

The GenBank accession numbers for s1 and s1' are U30166 and U30167, respectively.

DETAILED DESCRIPTION OF THE PREFERRED EMBODIMENTS

The present invention arises from the discovery of at least three satellite RNA sequences that are isolated from *Trichomonas vaginalis* infected with the dsRNA virus (TVV). These satellite sequences have been designated s1, s1' and s2. In addition, the satelike sequences are shown to be produced by the RNA dependent RNA polymerase (RDRP) activity inherent in TVV. This discovery, therefore provides an opportunity to insert a foreign gene into a *T. vaginalis* parasite that is infected with TVV. Because the s1 and s1' sequences have been produced as cDNA, these molecules may be used as a vector to transport foreign DNA that has been inserted into the cDNA, and transform TVV infected *T. vaginalis*. This discovery will thus provides the ability to insert gene markers, antisense or even mutant forms of *T. vaginalis* genes among others into the *T. vaginalis* parasite.

As a part of the present discovery, a relationship between the dsRNA virus (Khoshnan, A. and J. F. Alderete, 1993; Wang, A. and C. C. Wang, 1986)and phenotypic variation of the protein P270 (Alderete et al., 1986; Alderete et al., 1987; Alderete et al., 1986; Dailey, D. C. and J. F. Alderete, 1991) has previously been found. Disclosed herein, is evidence suggesting that this relationship is due to an increase in the level of P270 mRNA. Loss of the dsRNA virus, which occurs during in vitro cultivation of some isolates (Wang et al., 1987), results in the absence of detectable P270 mRNA. The presence of P270 protein in V⁻ trichomonads, however, does indicate that transcription and translation of the P270 gene occurs in all *T. vaginalis* organisms.

The exact mechanism(s) by which the presence of dsRNA influences or regulates levels of P270 mRNA is unknown. It is contemplated that the virus may upregulate P270 expression at the transcriptional level. This is because of the accumulation of P270 mRNA in only the V⁺ trichomonads and presence of low levels of P270 protein in the V⁻ progeny. Recently, this virus was found to have a multi-segmented genome (Khoshnan, A. and J. F. Alderete, 1993), increasing the coding capacity of this virus in comparison to other protozoan dsRNA viruses (Stuart et al., 1992; Wang, A. L. and C. C. Wang, 1991). Therefore, the virus may encode regulatory proteins which influence the expression of trichomonal genes. It is noteworthy that regulatory proteins responsible for modulation of phenotypic expression of a number of virulence-associated properties have been described for the dsRNA virus infecting *Endothia parasitica*, the fungal pathogen of the chestnut (Larson et al., 1992; Nuss, D. L., 1992). This precedence reinforces the idea that TVV may encode for regulators of transcription of *T. vaginalis* genes like P270.

An alternative explanation for the inability to detect the P270 mRNA in V⁻ organisms is that the turnover of mRNA is much greater in V⁻ than V⁺ parasites. In this scenario, V⁺ trichomonads may possess factors, either of host or viral origin, which inhibit mRNA degradation. This would allow for more stability and an extended half-life of mRNA, which would yield greater amounts of mRNA in the V⁺ trichomonads.

The molecular characterization of TVV, and its mechanism of replication is not fully understood. However, presented herein is evidence for RDRP activity of the virus with synthesis of products in vitro. Therefore, like other protozoan dsRNA viruses (Weeks et al., 1992; White, C. T. and C. C. Wang, 1990; Widmer et al., 1990), TVV particles possessed RDRP activity in vitro. The polymerase products were present in several fractions of the CsCl gradient, suggesting the existence of different enzyme complexes.

Two of the products, s1 and s2 were characterized further. The results of this analysis revealed that the in vitro polymerase products of s1 and s2 were double-stranded, and consistent with this finding, only one strand of s1 was synthesized in vitro by purified virus particles (See Example 5). From these observations, it appears that viruses in these assays contained single-stranded intermediates of the s 1 and possibly of the s2 genomes, which were converted to double-stranded forms by virus polymerase. As such and by analogy to replication mechanisms of other dsRNA viruses (Weeks et al., 1992; White, C. T. and C. C. Wang, 1990; Wickher, R. B., 1992; Widmer et al., 1990), the assays allowed for only the replicase or the dsRNA-synthesizing activity, of the TVV polymerase. It is important to optimize for conditions which will allow the synthesis of the opposite-strands of s1 and s2 in order to confine these possibilities.

Surprisingly, the synthesis of s1 and s2 dsRNA led to the discovery of new genetic material in infected *T. vaginalis*. These newly identified s1 and s2 behaved like dsRNA, as evidenced by resistance to degradation by RNase A and T1 under high salt. Banding on CsCl gradients and the ability to be synthesized in vitro by virus RDRP suggest that s1 and s2 associate with virus particles. Whether they are packaged with the parental L, M and S dsRNA segments (Khoshnan, A. and J. F. Alderete, 1993) or are carried separately remains unknown.

The absence of cross-hybridization between the parental dsRNAs and s 1 and s2 further showed that these unique dsRNAs do not share extensive sequence homology and, therefore, are unlikely to be defective-interfering (DI) RNAs. This was important to demonstrate, since a small DI genome has, in fact, been previously identified in some isolates of *T. vaginalis* (Tai et al., 1993). However, the data herein suggest that maintenance of s1 and s2 is dependent on the replication machinery provided by TVV. First, s1 and s2 were detected only in association with the parental virus. Also, s1 and s2 dsRNAs, along with RDRP activity, were never detected in the virus-minus trichomonads. Finally, elimination of the parental virus by extended in vitro cultivation (Wang et al., 1987) resulted in the concomitant loss of s1 and s2 (Khoshnan, A. and J. F. Alderete, 1994). Therefore, although s1 and s2 are distinct from the L, M and S dsRNA segments (Khoshnan, A. and J. F. Alderete, 1993), it is likely that they share some sequence or structural similarity that are essential for replication and encapsidation.

Of special interest was that amplification and, therefore, visualization in EtBr-stained gels of these new dsRNAs occurred only under controlled, continuous-flow culture, although no observable changes in the level of parental dsRNAs were seen, in either batch or chemostat conditions. These findings indicate that maintenance of s1 and s2, in addition to parental virus, also requires additional modulators that are more abundant under constant chemostat conditions. In contrast to batch cultures with $t_d$s of 2 h to 6 h (Lehker, M. W. and J. F. Alderete, 1990), it may be that any or all of the conditions in the chemostat, such as nutrient limitation, a prolonged $t_d$ (>24 h), and a constant pH of 5.5, favors accumulation of these regulatory factors that promote synthesis of s1, s2 and possibly the 1700 bp dsRNA in the *T. vaginalis* isolate 06201. Inability to visualize s1 and s2 in EtBr-stained gels of dsRNA obtained from batch culture parasites suggest low levels and transient replication under these conditions, something difficult to determine considering the growth kinetics of batch cultures. Conditional synthesis of viral RNA has also been reported in yeast. It has been shown that temperature and availability of specific nutrients regulate expression of the W dsRNA and its derivative, the 20S RNA in *Saccharomyces cerevisiae* (Matsumoto et al., 1990; Rodriguez-Cousifio et al., 1991; Wesolowski, M. and R. B. Wickher, 1984). Furthermore, in the same organism, it has been demonstrated that expression of a large number of cellular genes affect the L-A dsRNA virus (Matsumoto et al., 1990) and the satellite M1 dsRNA propagations (Wickner, R. B., 1992). That replication of s1 and s2 is controlled by environmental cues is significant in that other dsRNAs may still exist in virus-infected trichomonads but may not be detected under batch culture and in chemostat conditions disclosed herein. Therefore, other dsRNAs within TVV-infected *T. vaginalis* may exist.

That not all *T. vaginalis* isolates with TVV contained detectable s1 and s2 under the conditions examined may be explained by two possibilities. One is the existence of diversity in the number of dsRNAs among virus-carrying *T. vaginalis* isolates. A recent report indicated the presence of several dsRNAs associated with virus particles found in parasites of the genus Eimeria (Roditi et al., 1994). Of interest were two dsRNAs in *E. nieschulzi* with sizes of 0.7 kb and 0.57 kb, sizes similar to s1 and s2 of *T. vaginalis*. However, whether these segments are shared by all virus-harboring isolates is unknown. The presence of s 1 and s2 in some but not all virus-infected isolates, however, reinforces the idea that these smaller-sized dsRNAs are not prerequisite for maintenance of the parental dsRNA segments. As such, s1 and s2 and other dsRNAs may not be a part of the TVV genome.

The second possibility is that the new, smaller-sized dsRNAs may, in fact, be satellite RNAs parasitizing the parental virus for replication and assembly. Satellite dsRNAs are ubiquitous in yeasts and other fungi (Tipper, P. I. and M. J. Schmitt, 1992; Wickner, R. B., 1992), showing precedence for this possibility. The yeast M dsRNA satellite (~1.8 kb), which depends on L-A dsRNA virus for its maintenance, is known to encode the killer toxin and immunity to the toxin (Tipper, P. J. and M. J. Schmitt, 1992). It is noteworthy that, in *T. vaginalis* isolate 06201, a dsRNA of a size (~1700 bps) similar to that of the yeast dsRNA was amplified. Since s1 and s2 and the 1700 bp dsRNAs are conditionally synthesized and are present in only some of *T. vaginalis* isolates harboring the virus, it is contemplated that these amplified dsRNAs may be representative of satellite viruses.

The data presented here indicate that additional genetic information is being carried within virus-infected trichomonads. This further illustrates the complexity of the virus-parasite association and, ultimately, possibly even of the *T. vaginalis*-host relationship. Since the presence of this virus has been associated with phenotypic variation and virulence properties of trichomonads (Alderete et al., 1986; Khoshnan, A. and J. F. Alderete, 1994; Wang et al., 1987), it will be interesting to determine the products, if any, encoded by s1, s2 and the 1700 bp genetic elements and to examine whether they play a role in these processes. Further molecular characterization of these new dsRNAs will reveal information regarding the motifs on the genomes that are responsible for replication, transcription and assembly of the virus particles.

EXAMPLE 1 mRNA Levels Among $V^+$ and $V^-$ Isolates

Materials and Methods

Cultures

Parental isolates (P) with $V^+$ trichomonads were subjected to in vitro cultivation with daily passage in a complex medium (Alderete et al., 1986; Diamond, 1968). Progeny organisms without virus (N) were derived from numerous parental, agar-cloned trichomonads (Alderete et al., 1986) after extended in vitro passage as described (Diamond, 1968; Wang et al., 1987). During daily passage of cultures, trichomonads were examined for presence or absence of the virus.

Virus Particle Purification

Approximately $4 \times 10^9$ trichomonads were suspended in TNM buffer (50 mM Tris, pH 7.5, 150 mM NaCl and 5 mM $MgCl_2$) and sonicated until more than 90% of the cells were lysed. The lysate was clarified by centrifuging twice at 10,000× g for 20 min in a Sorvall SS34 rotor. The supernatant was then pelleted through a 20% sucrose cushion prepared in TNM buffer at 100,000× g in a SW40 rotor for 2 h. The sediment containing the virus particles was suspended in TNM buffer, equilibrated to a density of 1.35 g/ml with CsCl, and re-centrifuged at 100,000× g for 24 h. Twelve or twenty-four fractions of 1 ml or 0.5 ml each (respectively) were collected from the bottom of each tube and extensively dialyzed in TNM buffer. The fraction with the lightest density was labelled number 1.

One milliliter of each fraction was then treated with proteinase K (50 µg/ml) and 1% SDS at 65° C. for 30 min followed by phenol-chloroform extractions. The total RNA was precipitated with three volumes of ethanol and separated in a 1% agarose gel and stained with ethidium bromide (EtBr). dsRNAs migrated at 5.0 kb (Khoshnan and Alderete, 1993). This band was always absent from total nucleic acid preparations derived from the $V^-$ progeny. Absence of viral genomes were also confirmed by Northern analysis.

Fractions containing the viral RNA were further examined for the presence of virus particles by negative staining, and electron microscopy as described previously (Wang, A. and C. C. Wang, 1986).

Extraction and Analysis of dsRNA

All general RNA and DNA manipulations were as described in Maniatis et al., (1982). The dsRNA from infected trichomonads was extracted from total RNA (Chomczynski and Sacchl, 1987) treated with RNase T1 (10 U/µg) in the presence of 500 mM NaCl for 20 min, followed by three rounds of phenol-chloroform extraction. The dsRNA was precipitated with 3 volumes of ethanol. Electrophoresis of viral RNA in 1% agarose was performed as described previously (Khoshnan and Alderete, 1993).

For cross-hybridization studies, L, M and S dsRNA segments of TVV (Khoshnan and Alderete, 1993) and s1 and s2 were optimally separated in 1% low melting-point agarose using a Max Submarine Gel apparatus (Hoefer Scientific Instrument, San Francisco, Calif.). Individual segments were excised and treated with agarose enzyme (New England Biolabs, Inc., Beverly, Mass.) according to the manufacturer's instructions. The nucleic acids were precipitated with three volumes of ethanol.

Northern Blotting

Total RNA was isolated from fresh isolates of *T. vaginalis* by the methods described above. Approximately 15 µg of RNA from each isolate was resolved by denaturing formaldehyde agarose gel electrophoresis (Maniatis et al., 1982). RNA was then transferred to zeta probe nylon membrane in 50 mm NaOH (Bio-Rad Laboratories, Richmond, Calif.). Membranes were pre-hybridized for 2 hr at 42° C. in a solution having 50% formamide, 100 mM $Na_2PO_4$, pH 7.0, 125 mM NaCl, 7% SDS, 100 µg/ml salmon sperm DNA, and 20 µg/ml yeast RNA. Hybridization was carried out overnight at 42° C. in the same solution containing $10^7$ cpm of nick-translated [$\gamma$-$^{32}$P]dCTP-labelled P270 cDNA probe. Membranes were then washed sequentially for 3 min in 2× SSC (1× SSC contains 150 mM NaCl and 15 mm $Na_3$ citrate, pH 7.0) -0.1% SDS, 0.5× SSC-0.1% SDS and 0.1× SSC-0.1%, SDS at 65° C. and exposed to Kodak XAR-5 X-ray film.

To detect the presence or absence of viral genomes in trichomonads, riboprobes generated to the three dsRNA segments of the virus genome (Khoshnan and Alderete, 1993) were used. Hybridization was performed in the presence of [$\gamma$-$^{32}$p] CTP labelled riboprobes generated from a cDNA cloned in a pGEM32F(-) carrying the SP6 and T7 promoters (Promega Corp., Madison, Wis.). No hybridization signals were ever detected in Northerns using total RNA from the V⁻-progeny.

Results

To establish whether the presence of TVV affected overall expression of P270, it was first decided to use a recently generated cDNA, which encodes the repeat sequence of P270 (Dailey and Alderete, 1991), as a probe to evaluate mRNA levels among V⁻ and V⁺ isolates. P270 mRNA was detected in V⁺ and V⁻ isolate trichomonads by Northern blotting. Only blots with total RNA from V⁺ isolates for a representative V⁺ isolate (T068-II), had a detectable band for P270 mRNA. A 9.0 kb mRNA for P270 has been previously described (Dailey and Alderete, 1991). Under the same conditions, no bands were evident for any of the V⁻ isolates (SA92–80, T076, T077 and T080) when total RNA was examined under identical experimental conditions. As controls, the duplicate gels of ethidium bromide (EtBr)-stained total RNA were used to confirm that equivalent amounts of RNA were added to each well. These data suggest a possible relationship between accumulation and, therefore, detection of mRNA for P270 and the presence of the dsRNA virus in trichomonads.

To extend these initial observations, several *T. vaginalis* isolates were cloned in soft agar (Alderete et al., 1986) and grown for extended periods of time in order to obtain cloned V⁻ progeny (Wang et al., 1987). Criteria used to assign whether trichomonads either have or do not have TVV are as shown in Table 1. First, no detectable virus particles could be purified by CsCl (Khoshnan and Alderete, 1993; Wang, A. and C. C. Wang, 1986) from V⁻ organisms, as was readily done for V⁺ parasites under identical experimental conditions. Second, no dsRNA bands were visible by EtBr staining of agarose gels after total nucleic acid electrophoresis of V⁻ progeny organisms (Khoshnan and Alderete, 1993; Wang, A., and C. C. Wang, 1986; Wang et al., 1987). This method has been routinely used to show the presence of TVV in trichomonads (Wang, A. and C. C. Wang, 1986). Finally, the viral genomes were not detected by Northerns using riboprobes of recently generated cDNAs to each of the dsRNA segments in any of the V⁻ isolates or progeny (Khoshnan and Alderete, 1993).

Northern blot analysis revealed bands only in V⁺ parasites. This RNA species was not detectable in any of the samples of V⁻ progeny trichomonads when equal amounts of total RNA was examined simultaneously under the same experimental conditions. Furthermore, even addition of greater amounts of total RNA of V⁻ organisms in Northerns failed to give a signal. These data were in agreement with those described above in that loss of TVV resulted in reduction of P270 mRNA synthesis or a lack of accumulation possibly due to increased mRNA turnover. The size polymorphism of the P270 mRNA was not surprising and was consistent with the known heterogeneity of P270 molecular weights (Alderete et al., 1986).

TABLE 1

Presence or absence of TVV in *T. vaginalis* isolates

| | Detection of: | |
|---|---|---|
| Isolates | viral particles* | viral genome§ |
| parental V+ | | |
| AL8P | + | + |
| AL10P | + | + |
| 347P | + | + |
| 8111P | + | + |
| progeny V– | | |
| AL8N | – | – |
| AL10N | – | – |
| 347N | – | – |
| 8111N | – | – |

Parental isolates (P) with V⁺ trichomonads and progeny organisms without virus (N). During daily passage of cultures, trichomonads were examined for presence or absence of the virus as described in Example 1.
*Virus particles were purified by CsCl density gradients and observed by electron microscopy. The existence of viral particles was confirmed by detection of viral RNA in agarose-gels.
§Two methods were used to detect the segmented viral dsRNAs in trichomonads: examination for the presence of viral dsRNA genomes was by agarose-gel electrophoresis and EtBr staining of the total nucleic acid, as above; and Northern blotting using riboprobes generated to the three dsRNA segments of the virus genome (Khoshnan and J. F. Alderete, 1993).

EXAMPLE 2

P270 Protein Synthesis Among V⁺ and V⁻ Isolates

Materials and Methods

Immunoblots

Total cell proteins from $2 \times 10^6$ trichomonads were precipitated with $10^9$ trichloroacetic acid at 4° C. as described previously (Alderete et al., 1986), followed by solubilization in dissolving buffer (125 mm Tris-HCl, pH 8.0 149 SDS, 20% glycerol and 5% $_2$-mercaptoethanol) and boiling for 5 min prior to SDS-PAGE in a 7.59 acrylamide gels by standard procedures (Laemmli, U.K., 1970). Following separation, proteins were blotted onto nitrocellulose by electroblotting in 20 mM Tris-HCl, pH 8.0, 150 mM glycine and 20% methanol. Membranes were treated with a solution of 5% non-fat-dry-milk powder, and reacted with a mAb C20A3 (Alderete et al., 1986). A secondary goat-anti mouse antibody conjugated to horseradish peroxidase (Sigma) was then added, and membranes were developed according to established procedures. All other materials and methods were as described in Example 1.

Results

Since trichomonads of fresh clinical V⁻ isolates synthesize a low level of P270 proteins (Alderete, J. F. and K. A. Neale, 1989), it was essential that the V⁻ progeny with no detectable P270 mRNA also be examined for synthesis of the protein immunogen. This was accomplished by immunoblot analysis to detect P270 from V⁺ and V⁻ trichomonads after SDS-PAGE. V⁻ organisms were shown to still synthesize decreased amounts of P270 when compared to V⁺ organisms. This was evidenced by immunoblot analysis of the total lysate with the mAb C20A3 that recognizes the single repeated epitope of P270 (Alderete, J. F. and K. A. Neale, 1989; Dailey, D. C. and Alderete, 1991). Degradation, visualized by the appearance of multiple bands and smearing in immunoblots of the native P270, was described previously (Alderete, J. F. and K. A. Neale, 1989) and shown to be due to autodegradation of the protein by trichomonad proteinases (Alderete, J. F. and K. A. Neale, 1989; Coombs, G. H. and M. J. North, 1983; Neale, K. A. and Alderete, 1990) released during processing. The complex total protein patterns of Coomassie brilliant blue-stained gels of identical cell numbers indicate that equivalent amounts of protein were loaded for the V⁺ parental and V⁻ progeny samples. These results reaffirmed earlier observations with other isolates (Alderete et al., 1986; Alderete et al., 1987; Alderete et al., 1986; Alderete, J. F. and K. A. Neale, 1989) that P270 protein was expressed at higher amounts in V⁺ (Type II) parasites and that loss of the virus resulted in concomitant decreased synthesis of C20A3 immunoreactive proteins (Alderete, J. F. and K. A. Neale, 1989).

EXAMPLE 3

P270 gene Among V⁺ and V⁻ Isolates

Materials and Methods

Southern Blotting

DNA (10 μg) extracted from parasites was digested to completion with HindIII (Dailey, D. C. and Alderete, 1991). After separation by electrophoresis and transfer to nylon membranes, the DNA was probed with the 330 bp cDNA. Hybridization conditions and other materials and methods were as described in Example 1.

Results

Although all isolates made proteins immunoreactive to mAb C20A3 (Alderete et al., 1986; Alderete et al., 1987; Alderete et al., 1986), it was equally important to establish that the P270 gene was present in all V⁺ and V⁻ parasites. This was done by Southern blot analysis using as probe the 330 bp HindIII cDNA that encodes for the epitope that is tandemly repeated twelve times in the gene (Dailey, D. C. and Alderete, 1991). The Southern blot provided evidence that the gene was indeed present in all V⁺ isolates and V⁻ progeny trichomonads. The same intensity in hybridization was detected in all lanes of the gel containing DNA from either V⁺ or V⁻ parasites.

Finally, consistent with earlier work (Alderete et al., 1986; Wang et al., 1987), flow-cytofluorometry revealed that all V⁺ parental isolates had organisms which expressed P270 on the surface and underwent phenotypic variation. Under the same conditions, V⁻ progeny remained unable to place P270 on the surface during an extended period of evaluation.

EXAMPLE 4

RNA-dependent RNA Polymerase (RDRP) Activity of TVV Particles

Materials and Methods

Cultures

*T. vaginalis* designated T068-II, T042 and 06201 were fresh clinical isolates that were grown at 37° C. in the trypticase-yeast extract-maltose (TYM) medium supplemented with 10% heat-inactivated horse serum (Diamond, L. S., 1968) and harvested in the late-logarithmic-phase of growth for all studies. Agar clones such as T068-IIC1 used here were derived from single trichomonads of isolate T068-II as described recently (Alderete et al., 1986; Khoshnan and Alderete, 1993). Isolates NYH 286 and IR 78 are long-term-grown laboratory strains (Alderete et al., 1987; Alderete et al., 1986; Lehker, M. W. and Alderete, 1990) with and without TVV, respectively.

The virus particles were purified as described in Example 1, above. For generation of active replicase, the virus material present in the gradient was dialyzed in a low ionic strength buffer (1 mM Tris-HCl [pH 7.5], 1 mM EDTA, and 5 mM 2-mercaptoethanol) in order to obtain empty particles (Chen et al., 1994, Fujimura et al., 1988). The released RNA was removed by centrifugation at 100,000× g on a 10 to 40% continuous sucrose gradient made in TNM buffer in a SW40 rotor for 2 hours. The empty particles were harvested from the top gradient fractions, diluted in 12 volumes of TNM buffer, and pelleted by centrifugation as described above. Particles devoid of any detectable viral RNA but containing active RDRP were also obtained from a cytoplasmic fraction treated with the low ionic strength buffer, followed by centrifugation at 100,000× g in the CsCl gradient as described above. Fractions of the gradient with a density of ~1.28 to 1.30 were harvested and diluted in TNM buffer. The polymerase complex was then pelleted by centrifugation as described above.

RDRP Assay

RDRP activity of virus particles was assayed as described for the yeast dsRNA viruses (Fujimwa et al., 1986, Khoshnan et al., 1994). TVV particles from 1 ml of CsCl gradient fractions were diluted in TNM, pelleted by centrifugation at 100,000× g, and suspended in 100 μl of buffer A (50 mM TRis-HCl [pH 7.5], 20 mM NaCl, 5 mM MgCl$_2$, 0.1 mM EDTA, 5 mM KCl, 1 mM ATP, 1 mM CTP, 1 mM GTP, 1 mM UTP, 25 μCi [α-$^{32P}$]UTP, and 50 U/ml of RNasin). Reactions were incubated at 37° C. for 0.5 hour followed by addition of 5 mM EDTA and 0.5% SDS. Nucleic acids were extracted by phenol-chloroform treatment and precipitated in the presence of 1 volume of 4M ammonium acetate and 3 volumes of ethanol (Sambrook et al., 1989), and/or filtered through a CL-4B spin column (Pharmacia, Alameda, Calif.) to remove unincorporated nucleotides. After precipitation in the presence of 4M ammonium acetate and ethanol, synthesized transcripts were electrophoresed in 1% agarose, and the gel was then fixed in 7% trichloroacetic acid (Maniatis et al., 1982). Gels were dried for exposure to Kodak XRP-5 X-ray film. As a control, extracts of *T. vaginalis* isolates without TVV were fractionated and assayed under similar experimental conditions. The absence of TVV in some trichomonal isolates was confirmed by the same criteria as described in Table 1. RNase protection assays of polymerase products of a selected fraction was carried out with RNase A (50 µg/ml) in the presence of 50 mM or 600 mM NaCl at 37° C. for 20 min. Products were then recovered by phenol-chloroform extraction and evaluated as above. All other materials and methods were as described in Example 1.

Results

The present example demonstrates RDRP activity associated with TVV, as has been done for other protozoan and yeast dsRNA viruses (Fujimwa et al., 1986; Weeks et al., 1992; White, C. T. and C. C. Wang, 1990; Widmer et al., 1990). Prior to polymerase assays, CsCl fractions were first examined for the presence of viral dsRNAs by riboprobing as described in Example 1. Aliquots of CsCl fractions were probed for the presence of viral RNA by Northern blot analysis. Processing of RNA and hybridization conditions for each fraction were described in Examples 1, 5 (respectively). Labelled probes were generated by in vitro transcription from pV15 (Khoshnan and J. F. Alderete, 1993), a partial cDNA of M segment cloned in PGEM3Zf. A single fraction (10) gave the most intense bands after autoradiography. Similar patterns were observed when cDNAs of L and S were used as probes.

Upon analysis of in vitro polymerase products of the same CsCl fractions as described in the previous paragraph by Northern analysis using as probe a partial cDNA to the M segment (Khoshnan and Alderete, 1993), evidence for viral RNA in fractions which also had detectable polymerase activity (Fujimwa et al., 1986; Khoshnan and Alderete, 1993; Khoshnan and Alderete, 1994; Khostman and Alderete; Lehker, M. W. and Alderetc. 1990; Maniatis et al., 1982; Matsumoto et al., 1990). Such RDRP activity was measured by the ability to incorporate radiolabeled [α-$^{32}$P] CTP in vitro. Analysis of the assays by autoradiography showed synthesis of transcripts comigrating with the three dsRNA segments of the virus (described as Fraction 10 in the preceding paragraph), as well as other smaller RNAs synthesized by all fractions (Fujimwa et al., 1986; Fujimwa et al., 1986; Khoshnan and Alderete, 1993; Khoshnan and Alderete, 1994; Khoshnan and Alderete; Lehker, M. W. and Alderete. 1990; Maniatis et al., 1982; Matsumoto et al., 1990). Two transcripts migrating at ~700 bp (s1) and ~500 bp (s2) were predominant products. These assays revealed that, like other dsRNA viruses, TVV particles contain RDRP activity. Importantly, RDRP activity was never detected from similar fractions obtained from lysates of trichomonads without detectable TVV (Khoslman and Alderete, 1993), confirming the viral origin of this enzyme activity.

EXAMPLE 5

Cloning and Nucleotide Sequencing of s1 and s1' cDNA

Materials and Methods

S1 and s1' were separated from total dsRNA by electrophoresis in low melting point agarose gels. Approximately 1 µg of satellite dsRNA was polyadenylated in vitro with *Escherichia coli* poly(A) polymerase (GIBCO BRL, Gaithersburg, Md.) according to the manufacturer's instructions. The average length of the poly(A) tail was determined by sequencing to be around 16 bases. The poly(A)-tailed RNA was denatured by boiling for 3 minutes and was reverse transcribed in a reaction buffer containing 50 mM Tris-HCl [pH 8.3]; 40 mM KCl; 6 mM MgCl$_2$; 1 mM dithiothreitol; 0.5 mM [each] dATP, dCTP, cGTP, and dTTP; 0.1 mM oligo (dT); 0.1 mg of bovine serum albumin per ml; and 24 U of avian myeloblastosis virus reverse transcriptase (GIBCO BRL) and incubated for 40 minutes at 50° C. The RNA-DNA hybrid was treated with 1 U of ribonuclease H at 12° C. for 1 hour. Second strand DNA synthesis was carried out in the presence of 115 U of DNA polymerase I and with incubation at 22° C. for 1 hour. The reactions were stopped by incubation at 70° C. for 10 minutes and the cDNA was blunt ended with 1 U of T4 DNA polymerase at 37° C. The purified cDNA was cloned into the Sinai site of linearized pGEM4Z (Promega Corporation, Madison, Wis.) cloning vector. The recombinants were transformed into competent *E. coli* JM109 cells. Positive clones were selected by insert analysis and confirmed by Northern (RNA) analysis. Two clones labeled pVss18 and pVss10, for the s1 and s1' satellite RNAs, respectively, were used for the studies described herein.

The nucleotide sequence determination was performed twice for both strands of the cDNA clones by the dideoxy-chain termination method (Sanger et al., 1977) with automated DNA sequencing. Sequence analysis was performed with PC Gene computer software.

Northern Blotting

Viral dsRNAs (~1 µg) or total RNA from *T. vaginalis* IR 78, and T080 (~10 µg), two virus-minus isolates, were electrophoresed into a non-denaturing 1% agarose gel and blotted onto a Zeta probe nylon membrane (Bio Rad Laboratories, Inc., Richmond, Calif.) in the presence of 50 mM NaOH according to the manufacturer's instructions. In order to characterize the products of the RDRP assay, cDNA was synthesized for s1 dsRNA and cloned into the transcription vector pGEM4Z (Khoslman and Alderete, 1993). Transcripts were generated from the T7 and SP6 promoters and treated similarly. Probes for hybridization were generated by the RDRP assays described in Example 4 using purified virus particles, or as described below.

Cloning of partial cDNAs of viral dsRNA segments in pGEM3Zf was reported previously (Khoslman and Alderete, 1993). Riboprobes were obtained by in vitro transcription using T7 polymerase in the presence of [α-$^{32}$P]CTP, according to the manufacturer's recommendation (Promega Corporation, Madison, Wis.). For cross-hybridization analysis, the parental L, M and S dsRNAs (Khoshnan and Alderete, 1993) and the newly discovered segments s1 and s1' (described here) were labelled by random-priming with AMV reverse transcriptase (Promega) in the presence of [α-$^{32}$P]dCTP and [α-$^{32}$P]dTTP (Khoshnan and Alderete, 1993). All of the generated probes were denatured by boiling for 5 minutes in the presence of 4M urea and 20 mM EDTA prior to use. Hybridizations were performed overnight in the presence of 50% formamide, 100 mM Na$_2$PO$_4$, pH 7.0, 125 mM NaCl and 7% SDS at 42° C. Filters were washed sequentially for 30 min each time in 2× SSC (1× SSC contains 0.15M NaCl and 0.015M Na$_3$citrate, pH 7.0)- 0.1% SDS, 0.5× SSC-0.1% SDS, and 0.1× SSC-0.1% SDS at 65° C. (Matsumoto et al., 1990) and exposed to X-ray film.

Alternatively, total RNA from infected trichomonads was obtained by the methods of Chomzynski and Sacchi (1987). Single stranded RNA was separated by treatment of total RNA with 2M LiCl and incubation at 4° C. for 4 hours followed by centrifugation at 10,000 rpm for 10 minutes in a microcentrifuge (Sambrook et al., 1989) and approximately 10 µg of ssRNA was electrophoresed into a denaturing 1% agarose gel. RNA was then transferred to zeta probe nylon membrane in 50 mm NaOH (Bio-Rad Laboratories, Richmond, Calif.). Membranes were prehybridized for 2 hr at 55° C. in a solution having 50% formamide, 100 mM $Na_2PO_4$, pH 7.0, 125 mM NaCl, 7% SDS, 100 μg/ml salmon sperm DNA, and 20 μg/ml yeast RNA. Hybridization was carried out overnight at 55° C. in the same solution containing $10^8$ cpm of radiolabeled riboprobes generated from the s1 and s1' cDNA clone linearized with BamHI and transcribed with SP6 RNA polymerase. Membranes were then washed sequentially for 30 minutes each time in 2× SSC (1× SSC contains 150 mM NaCl and 15 mm $Na_3$ citrate, pH 7.0) - 0.1% SDS, 0.5× SSC-0.1% SDS and 0.1× SSC-0.1%, SDS at 55° C. and exposed to Kodak XAR-5 X-ray film.

RNase protection assays were performed on s1 transcripts replicated in vitro by treating with RNase T1 (50 U/ml) in the presence of 50 or 500 mM NaCl and with incubation at 37° C. for 30 minutes. The reactions were stopped by addition of 5 μl of 500 mM EDTA. The products were extracted with phenol-chloroform and precipitated with ethanol. Analysis was by agarose gel electrophoresis and autoradiography.

For in vitro replication assays, s1 transcript was generated from the s1 cDNA clone (pVss18), linearized with EcoRI or BamHI, and transcribed with T7 or SP6 RNA polymerase, respectively. The integrity of the synthesized transcripts was assessed on a 1.5% agarose gel. Different quantities of RNA of opposite polarities were added to the reaction mixture. Incubation and processing were performed as described above.

All other materials and methods were as described in Examples 1 and 4.

Results

Full-length cDNAs of s1 and s1' satellites were obtained from the in vitro polyadenylated dsRNAs. The nucleotide sequences of the cDNAs are as follows.
The s1 cDNA sequence is:
CAGAGATATC GGTGCAAAAC CTGTACTGTT CCGCTCATGT CAAGATTGTG CTCGGGCGCT ACCCGTTACC AATCAGACAT GTGGTTTATT TCACCTACCC CACGGCAAGG CAGGACACAG AGTACCCCTG AGACGCACAG ACATATGCAT TATCCCTACT ATCTGCGACA CTTACTCTTC GTCACCCACA ATGACGTCTA CAAAATGCTC AAT- GTAAGAC CAACAACCAA GAGCCAGCTT ACGC- CCGCCC ATTATACTTG CTTTTAAAGC GGGAGT- TATG ATTGGCGGGA TAAAGAACAT AAGTAGCAAAAGAGTAAACA TCGCCATGAA TAGTACGGCT CAACACCTAG GACAACGTTA AGTCTAAGTAAAGCAGGTGG GTGGTTGACG AGACATCCAG TACCTAGAAC TCAACCAGAT GCCTCCCCCC TGTATTACTT CACTATTCAAAAG- CAGGTAT AGCATTCCCA TACCACAGAC TGCTC- GATGT GAGTCGACCA GAGAGGGCGC TGTAC- GAACC TGAACTATAG ACGCGCTCCA GCATAGGCTG GCCAAAAAAG G CTCATTCTT CCTCACAGAA GAATGCATTA CCGC- CTATCC CGGGGCTACG TCAGATAGTT GGTGC- CGGGA CACTCGTATA TGGTTTACAC CGATATA- CAC TTAAAGACTT CCTATCGCTT CTTTAAGC, SEQ ID NO:1.
The s1' cDNA sequence is:
CGTGTTCAGG GACGTTGCCA CAAGCACGGG TCG- TACCTCC CATCCTTAGC GGTTTTGACC AACTA- CAAGG ACACGCATCC GAGACAGAGC TCCT- GCGTCC AGGTATTAGC CCGCTATCTA ACACGCTAGC GTTTTAGAGA CTGACGTCAA TAGCCTTTAC CTACGCAAAC AGAGCCCCCT CTTCAACATG CCCACATTGA TCTCAACGAG CCGGGGTACC GACATGGGAC TTCACTCTCA CCGCGTCATT ACGACCTGTA GGTACCTATT ACAGTAACGT CTGGGTCTAG CACTCGGTTT GAACCAAGAT TCGCTATGGG TCGGCAGTCG ACTCGGGGTG AGCAGTCCCG AGGCCCCCTT TTGCGCAACG CTGTCCGTAG TTTCGTGATA CAG- GCGATGT ACTGTGCCCC TAACCCCCGT CCGC- CCCATT GCGCCGAACC TCGGTAGCTT TCGACTCTGT ACCCTAATAC TACGACACAT ACCCAGAAAG       CGATTTCAC CTCATTCTTCC GCAGTAGAGA      GATTCCATTG GATGTAGGTG CCCATACATT ACGTATGAGA ATACTACCGG ATACGCGACG CCCGGTAGGC CTAAAAATCA TTTCAGGTTT TTAAGC, SEQ ID NO:3.

The ends for each segment were confirmed by sequencing of cDNA clones that were polyadenylated at the 3' ends of the opposite strands. The sizes of the cDNAs were consistent with those estimated from agarose gels (Khoshnan et al., 1994). The s1 and s1' dsRNAs contained G+C contents of 48 and 52%, respectively. The 7 nucleotides at the 3' end of both s1 and s1' contained the sequence 5'-TTTAAGC-3' (underlined in the sequences listed above). A second conserved domain with the nucleotide sequence of 5'-CTCATTCTTCC-3', SEQ ID NO:17 (underlined in the sequences listed above) is also present at ~100 nucleotides upstream of the 3' end of both s1 and s1'. A potential open reading frame (ORF) on the putative sense strand of s1 begins at nucleotide 37 and terminates at nucleotide 264. No homology with any known sequence has been discovered by the inventor at the nucleotide or amino acid level for the putative protein encoded by the potential ORF. No similar ORF is apparent for s1'.

EXAMPLE 6

Replication of s1 and s1'

Northern blot analysis was performed to determine whether the synthesized transcripts were originating from the virus dsRNA segments (Khoshnan and Alderete, 1993). Total dsRNA obtained from the T068-IIC1 trichomonads were probed with the in vitro RDRP-generated s1 and s2 polymerase products, generated by fractions 6 through 9 (See Example 4). Probes were generated by the RDRP assay as described in Example 4, except that [α-$^{32}$P]CTP and [α-$^{32}$P]UTP were used together for labelling, and the incubation time was increased to 1 h. Surprisingly, these radiolabeled products did not hybridize to the parental dsRNA segments, but recognized other RNAs with mobilities similar to s1 and s2. When fraction 10 (Example 4) products were used as the probe, however, hybridization to the parental dsRNAs was observed. Longer exposer of X-ray film also showed some hybridization to bands comigrating with s 1 and s2. The labeled polymerase products did not hybridize to RNA obtained from IR 78, an isolate without the virus (Khoshnan and Alderete, 1993). These data indicated that additional dsRNAs may be replicating in the virus-infected trichomonads.

The replicative intermediates of the satellite RNAs were also characterized to determine whether their synthesis was also affected by stressed environments. Northern analysis was done with ssRNA obtained from batch and chemostat cultures of infected trichomonads by using the putative sense probes of s1 and s1'. A full-length, single stranded intermediate for each of the satellite RNAs was seen amplified only in parasites cultivated in the chemostat at extended generation times of 24 and 48 hours compared with similar amounts of ssRNA obtained from batch-grown trichomonads. Under identical conditions, s1 transcripts were present in larger quantities than s1' transcripts on the basis of the intensity of the bands, indicating differential amplification of the satellites. The opposite sense ssRNA strands were not detected. These data demonstrate the presence of a full-length ssRNA intermediate for the s1 and s1' RNAs and showed that up-regulation of transcription of satellite RNAs occurred under stressed conditions.

EXAMPLE 6

Amplification of s1 and s2 Occurs in Continuous-Flow Cultures

Materials and Methods

Chemostat Cultures

For the chemostat cultures, parasites from each isolate were centrifuged and resuspended in 10 ml of TYM medium. Organisms were inoculated into the growth-vessel containing TYM-5% serum to an initial cell-density of $1 \times 10^5$ cells $ml^{-1}$ (Lehker, M. W. and Alderete, 1990). Cultures were maintained aerobically at 37° C. at a dilution rate of 0.028 $hour^{-1}$ ($h^{-1}$), which corresponds to a doubling time ($t_d s$) of 24 h (Tempest, D. W., 1970). Following inoculation, cells were allowed to acidify the medium and were kept at pH 5.5, a pH relevant during trichomoniasis (Alderete et al., 1991). Motility, morphology, cell density of the cultures, and percent of dead cells were monitored by microscopy, as described (Lehker, M. W. and Alderete, 1990). Parasites from stabilized cultures were harvested periodically for each condition, washed three times in PBS, and used immediately or stored at −70° C.

All other materials and methods are as described in Examples 1, 4 and 5.

Results s1 and s2, possibly associating with TVV, were not readily visualized on EtBr-stained gels of viral dsRNA from batch-grown trichomonads. A similar analysis for the synthesis of s1 and s2 RNAs was being performed simultaneously on trichomonads cultivated in a chemostat. A comparison of the growth kinetics and environmental parameters between batch versus chemostat cultures was done. *T. vaginalis* T068-IIC1 in batch culture conditions had a $t_d$ of 2–6 hours during growth and multiplication, and the pH of the medium decreased continuously. An increase in the percent of dead organisms was evident at stationary phase (30 h). In contrast to batch culture conditions, chemostat-grown *T. vaginalis* T068-IIC1 parasites were maintained at a constant cell density with a $t_d$ 24 h and a pH 5.5. Minimal cell death was evident throughout the continuous-flow culture. Continuous addition of nutrients (medium) to the chemostat is in contrast to the depletion of nutrients and accumulation of metabolic end-products of batch cultures (Lehker and Alderete, 1990). In batch culture, growth parameters underwent continuous change in contrast to the chemostat in which conditions remained constant.

TVV from *T. vaginalis* T068-IIC 1 cells grown at a $t_d$ 24 h at pH 5.5 had levels of s 1 and s2 readily detectable by EtBr staining of agarose gels. For example, EtBr-stained gels of viral RNA had, in addition to the parental dsRNA segments, visible smaller dsRNAs corresponding to s1 and s2 (Fractions 7–12). When inocula from chemostat cultures were returned to batch conditions for several generations, EtBr-stained gels of equivalent amounts of RNA failed to give detectable s1 and s2. Thus, replication of s1 and s2 is unregulated in *T. vaginalis* T068-IIC1 grown in the chemostat. s1 and s2 associated with purified virus were readily visible in contrast to batch cultures. s1 and s2 were present in all fractions that had the parental dsRNAs.

Furthermore, virus preparations from the chemostat cultures were analyzed for RDRP activity as in Example 4. The products of the RDRP assay were analyzed under normal and denaturing (4M urea and 20 mM EDTA followed by boiling) conditions. The RDRP assay was performed exactly as in Example 4, and it is noteworthy that only one-tenth of the amount used in Example 4 was added to individual wells for electrophoresis and autoradiography. Examination of the synthesized products by several fractions revealed bands corresponding to s1 and s2. The band intensities were similar to those seen for the batch culture virus despite the fact that only one-tenth of the amount of purified virus from the chemostat was used. In addition, other smaller transcripts were also synthesized by these preparations. However, Northern blot analysis revealed hybridization of these products to only s1 and s2. The diminished synthesis of transcripts of the dsRNA segments was possibly due to the lower amounts of parental dsRNAs in the reaction, as seen in the EtBr-stained gels. However, enhanced exposure of the X-ray film revealed that fractions 10 and 11 contained transcripts comigrating with the large dsRNAs segments. This increased synthesis of s1 and s2 both in vivo and in vitro by virus particles obtained from continuous-flow cultures suggested the conditional synthesis of new RNAs. Numerous attempts to purify virus particles with only s1 and s2 by multiple rounds of CsCl density gradient centrifugations were unsuccessful.

When duplicate samples of the RDRP products were denatured by urea and heat (Weeks et al., 1992), the electrophoretic mobilities of the bands increased, indicating that synthesized s1 and s2 were possibly double-stranded. To further test this hypothesis the polymerase products of fraction 10 were treated with ribonucleases under high salt and low salt conditions. The products were readily degraded by RNase A (50 µg/ml) in the presence of 50 mM NaCl. The products were protected from RNase degradation when 600 mM NaCl was present in the reactions. This degradation only under low salt conditions indicates that s1 and s2 were double stranded.

In order to characterize further the in vitro-synthesized polymerase products of s1, RNAs of opposite polarities were obtained from the s1 cDNA and probed with the labeled polymerase products of fraction 8, 9 and 10 of Example 4. cDNA to s1 was generated from poly-A tailed s1 dsRNA and cloned into the transcription vector pGEM4Z as reported for other dsRNAs of this virus (Khoshnan and Alderete, 1993). Approximately 1 µg of plasmid carrying the s1 cDNA was linearized either with EcoRI or HindIII restriction enzymes and transcribed in vitro from the T7 or SP6 promoters, respectively. Transcripts were separated in 1% agarose under denaturing conditions, as described in Example 5. Total RNA of a virus-minus isolate T080 was included as a negative control to show the specificity of probes. The gel was transferred onto nylon membranes and hybridized with labeled polymerase products of fraction 8, 9 and 10. Procedures and conditions were as described in Example 5. Hybridization occurred only with the transcripts generated from the T7 promoter. Hybridization was not seen with either RNA of s1 obtained from the SP6 promoter (lane SP6) nor with total RNA extracted from the virus-minus isolate T080 (lane T080). These data suggest that only one strand of s1 was synthesized by virus particles in vitro.

EXAMPLE 7 s1 and s2 Are Not In All Isolates

Chemostat conditions also allowed for the direct detection of s1 and s2 without the need for virus purification. Therefore, an attempt was made to determine whether s1 and s2 were present among several isolates harboring TVV. Representative dsRNA profiles were obtained from several isolates cultivated under defined chemostat conditions. Total dsRNA was purified from RNA of chemostat-grown cultures by treatment with RNase T1 under high salt (500 mM NaCl) conditions. Approximately, $2 \times 10^6$ cell equivalents were electrophoresed in 1% agarose and stained with EtBr. Both s1 and s2 were not detected in all TVV-infected isolates. While s1 and s2 could readily be detected in an agar-derived clone, T068-IIC1, and its parental fresh clinical isolate, T068-II, isolate NYH 286, a long-term-grown culture, and T042, another clinical isolate, were without detectable s1 and s2. Absence of s1 and s2 in these isolates was further confirmed by Northern analysis using labeled polymerase products as a probe. Interestingly, cultivation of *T. vaginalis* 06201, which had fewer in vitro passages, had s1, s2 and another dsRNA element of ~1700 bp under similar conditions. A hint band of similar size was occasionally visible in the total dsRNA profile of T068-IIC1.

In some preparations, s1 appeared to migrate as a doublet. To test for this possibility, s1 was purified from a low-melting point agarose gel and re-electrophoresed for an extended period. s1 was thus further resolved into two distinct bands, s1 and s1'.

EXAMPLE 8 s1 and s2 Are Unique dsRNAs s1 and s2 were examined for homology to partial cDNAs cloned for L, M and S dsRNA segments (Khoshnan and Alderete, 1993). Riboprobes obtained from these cDNAs did not recognize the s1 and s2 dsRNAs by Northern analysis as performed by procedures described in Example 5. To further investigate the relationship between the parental dsRNAs, cross-hybridization studies were performed with s1 and s2 on total dsRNA from chemostat-grown parasites of T068-IIC1, using, as probes, radiolabeled gel-purified parental dsRNAs, s1 or s2. RNA from the virus-minus isolate IR 78 was used similarly as a control.

The dsRNA from T068-IIC1 and total RNA of isolate 1R 78 were probed with labelled parental ds RNAs. Procedures and conditions were as described in Examples 1 and 5. Probes were generated by reverse transcription of approximately 1 μg each of the dsRNAs in the presence of [α-$^{32}$P] dCTP and [α-$^{32}$P]TTP using hexanucleotide random primers. $^{32}$P-labeled parental dsRNA hybridized only to itself and not to either s1 or s2, which were present in the same lane.

Labeled s1 and s2 did not cross-react with the parental dsRNAs. Furthermore, hybridization studies using labeled s1 cDNA as probes were consistent with the absence of cross-hybridization between s1 and the parental dsRNAs. No detection of RNA from isolate IR 78, another virus-minus isolate, was evident throughout. In addition, no hybridization of s1 and s2 dsRNAs with total electrophoresed *T. vaginalis* genomic DNA from TVV-infected trichomonads was ever observed. Due to the close migration of s1 and s1', the relationship between them could not be determined. The 1700 bp genetic element from *T. vaginalis* isolate 06201 was resistant to labelling by reverse transcriptase. The studies above also showed that the 1700 bp element was not detected in total dsRNA of T068-IIC1 by labeled s1, s2 and parental dsRNAs used as probes. These data do show, however, that s1 and s2 are unique dsRNAs and are believed to encode information different from the L, M and S dsRNA segments.

EXAMPLE 9

Use of s1, s1' And s2 As Genetic Vectors for Transformation of *Trichomonas vaginalis*

The s1, s1' and s2 are small double-stranded RNA (dsRNA) satellites that are detected in some *T. vaginalis* isolates harboring a dsRNA virus. Propagation of s1, s1' and s2 is dependent on the enzymatic machinery provided by the virus. The vital genome, as well as the s1, s1' and s2 dsRNAs, must contain regulatory sequences. These sequences must be recognized by the RNA-dependent RNA polymerase of the virus, as has been shown for dsRNA viruses of other protozoa.

Since s1, s1' and s2 dsRNAs can be synthesized to high levels by the parental dsRNA viral polymerase, the complementary DNA (cDNA) of these satelike RNAs can be manipulated in vitro. By doing this, a construct incorporating the regulatory sequences of the satellite dsRNAs with foreign genes of interest and markers can be used as vectors. In this way it may be possible to introduce and express foreign genes in the virus-harboring *T. vaginalis*. Any gene of interest can be ligated to the regulatory sequences of either s1 or s1' dsRNA or s2, and, using standard techniques, the recombinant cDNA should be able to be introduced into *T. vaginalis* isolates carrying the virus. Replication of the gene of interest will then be under the control of virus RNA-dependent RNA polymerase.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alderete, J. F., "*Trichomonas vaginalis* phenotypic variation may be coordinated for a repertoire of trichomonad surface immunogens," *Infect. Immun.*, 55:1957–1962, 1987

Alderete and Kasmala, "Monoclonal antibody to a major glycoprotein immunogen mediates differential complement-independent lysis of *Trichomonas vaginalis,*" *Infect. Immun.*, 53:697–699, 1986.

Alderete and Neale, "Relatedness of structures of a major immunogen in *Trichomonas vaginalis,*" *Infect. Immun.,* 57: 1849–1853, 1989.

Alderete et al., "Phenotypes and protein/epitope phenotypic variation among fresh isolates of *T. vaginalis,*" *Infect. Immun.,* 55:1037–1041, 1987.

Alderete et al., "Monoclonal antibody to a major surface glycoprotein immunogen differentiates isolates and subpopulation of *Trichomonas vaginalis,*" *Infect. Immun.,* 52:70–75, 1986.

Alderete et al., "Phenotypic variation and diversity among *T. vaginalis* isolates and correlation of phenotype with trichomonal virulence determinants," *Infect. Immun.,* 53:285–293, 1986.

Alderete et al., "The vagina of women infected with *Trichomonas vaginalis* has numerous proteinases and antibody to trichomonad proteinases," *Genitourin. Med.,* 67:469–474, 1991.

Chomczynski and Sacchi, "Single-step method of RNA isolation by acid guanidinium thiocyanate-phenol-chloroform extraction," *Anal. Biochem.,* 162: 156–159, 1987.

Coorobs and North, "An analysis of the proteinases of *Trichomonas vaginalis* by acrylamide gel electrophoresis," *Parasitol.,* 86:1–6, 1983.

Dailey and Alderete, "The phenotypically variable surface protein of *Trichomonas vaginalis* has a single, tanden-fly repeated immunodominant epitope," *Infect. Immun.,* 59:2083–2088, 1991.

Diamond, L. S., "Techniques of axenic culture of *Entamoeba histolytica* schaudinn, 1903 and *E. histolytica*-like amoebae," *J. Parasitol.,* 54:1047–1056, 1968.

Fujimwa et al., "In vitro L-A dsRNA synthesis in virus-like particles from *Saccharomyces cerevisiae,*" *Proc. Natl. Acad. Sci. USA,* 83:4433–4437, 1986.

Khoshnan and Alderete, "Multiple double-stranded RNA segments are associated with virus particles infecting *Trichomonas vaginalis,*" *J. Virol.,* 67:6950–6955, 1993.

Khoslman and Alderete, "*Trichomonas vaginalis* with a double-stranded RNA virus has upregulated levels of phenotypically variable immunogen mRNA," *J. Virol.,* 68:4035–4038, 1994.

Laemmli, U. K. 1970. Cleavage of structural proteins during the assembly of the head of bacteriophage $T_4$. *Nature* 227:680–685.

Larson et al., "Regulatory pathways governing modulation of fungal gene expression by a virulence-attenuating mycovirus," *EMBO,* 11:4539–4548, 1992.

Lehker and Alderete, "Properties of *T. vaginalis* grown under chemostat controlled growth conditions," *Genitourin. Med.,* 66:193–199, 1990.

Maniatis et al., "Molecular cloning: A Laboratory manual," Cold Spring Harbor Laboratory, Cold Spring Harbor, N.Y., 1982.

Matsumoto et al., "Circular single-stranded RNA replicon in *Saccharomyces cerevisiae,*" *Proc. Natl. Acad. Sci. USA* 87:7628–7632, 1990.

Neale and Alderete, "Analysis of the proteinases of representative *Trichomonas vaginalis* isolates," *Infect. Immun.,* 58: 157–162, 1990.

Nuss, D. L., "Biological control of chestnut blight: an example of virus-mediated attenuation of fungal pathogenesis," *Micro. Rev.,* 56:561–576, 1992.

Patterson, J. L., "Viruses of protozoan parasites," *Exp. Parasitol.,* 70:111–113. 1990.

Plorde, J. J., "Medical Microbiology, An Introduction to Infectious Diseases", J. C. Sherris ed. Elsevier Science Publishing Co., Inc. New York, 1984.

Provenzano, D., and Alderete, J. F., Analysis of human immunoglobulin-degrading cysteine proteinases of *Trichomonas vaginalis*. *Infect. Immun.* 63:3388–3395.

Roditi et al., "Virus-like particles in Eimeria nieschulziare associated with multiple RNA segment." *Mol. Blochem. Parasitol.,* 63:275–282, 1994.

Rodriguez-Cousffio et al., "Molecular cloning and characterization of W double-stranded, a linear molecule present in *Saccharomyces cerevisiae,*" *J. Biol. Chem.,* 266: 12772–12778, 1991.

Stuart et al., "Molecular organization of Leishmania RNA virus 1," *Proc. Natl. Acad. Sci. USA,* 89:8596–8600, 1992.

Tai et al., "The divergence of *Trichomonas vaginalis* virus RNAs among various isolates of *Trichomonas vaginalis,*" *Exp. Parasitol.,* 76:278–286. 1993.

Tempest, D. W., "The continuous cultivation of microorganisms: 1. Theory of the chemostat". Methods in Microbiology. Norris, J. R., Ribbons, D. W. (eds.), London: Academic Press, pp. 259–276, 1970.

Tipper and Schmitt, "Yeast dsRNA viruses: replication and killer phenotypes," *Mol. Micro.,* 5:2331–2338, 1992.

Wang and Wang, "Viruses of the protozoa," *Annu. Rev. Microbiol.,* 45:251–263, 1991.

Wang et al., "*Trichomonas vaginalis* phenotypic variation occurs only among trichomonad infected with the double-stranded RNA virus," *J. Exp. Med.,* 166: 142–150, 1987.

Wang and Wang, "The double-stranded RNA in *Trichomonas vaginalis* may originate from virus like particles," *Proc. Natl. Acad. Sci. USA,* 83:7956–7960, 1986.

Wang and Wang, "A linear double-stranded RNA in *Trichomonas vaginalis,*" *J. Biol. Chem.,* 260:3697–3702, 1985.

Wang et al., "Giardia virus double-stranded RNA genome encodes a capsid polypeptide and a gag-pol like fusion protein by a translation frameshift," *Proc. Natl. Acad. Sci. USA,* 90:8595–8599, 1993.

Weeks et al., "LRV1 vital particles in *Leishmania guyanensis* contain double-stranded or single-stranded RNA," *J. Virol.,* 66:1389–1393, 1992.

Weeks et al., "Transcribing and replicating particles in a double-stranded RNA virus from Leishmania," *Mol. Biochem. Parasitol.,* 52:207–214, 1992.

Wesolowski and Wickher, "Two new double-stranded RNA molecules showing non-mendelian inheritance and heat inducibility in *Saccharomyces cerevisiae,*" *Mol. Cell. Biol.,* 4:181–187, 1984.

White and Wang, "RNA-dependent RNA polymerase activity associated with the double-stranded RNA virus of *Giardia lamblia,*" *Nuc. Acids Res.,* 18:553–559, 1990.

Wickher, R. B., "Double-stranded and single-stranded RNA viruses of *Saccharomyces cerevisiae,*" *Annu. Rev. Microbiol.,* 46:346–375, 1992.

Widmer et al., "RNA polymerase activity is associated with viral particles isolated from *Leishmania braziliensis* subsp. guyanensis," *J. Virol.,* 64:3712–3715, 1990.

What is claimed is:

1. An isolated nucleic acid comprising a contiguous sequence consisting of SEQ ID NO:1 or SEQ ID NO:3 or the full length complement of SEQ ID NO:1 or SEQ ID NO:3.

2. The isolated nucleic acid of claim 1, wherein said consists of the sequence of SEQ ID NO:1 or its full length complement, or SEQ ID NO:3 or its full length complement.

3. The isolated nucleic acid of claim 1, wherein said nucleic acid segment comprises a cDNA molecule.

4. A recombinant vector comprising the isolated nucleic acid of claim 1.

5. The recombinant vector of claim 4, wherein said vector replicates in a TVV infected *Trichomonas vaginalis* host.

6. A protozoan cell containing the recombinant vector of claim 4.

7. The protozoan cell of claim 6, wherein said cell is a *Trichomonas vaginalis* cell.

8. A method of expressing a recombinant gene in a TVV infected protozoan cell comprising the steps of:

(a) preparing a nucleic acid molecule comprising a recombinant gene fused with a sequence in accordance with SEQ ID NO:1 or SEQ ID NO:3;

(b) transfecting said molecule into a TVV infected protozoan cell; and (c) culturing said cell under conditions appropriate for the expression of said recombinant gene.

9. The method of claim 8 wherein said protozoan cell is a *Trichomonas vaginalis* cell.

10. An isolated nucleic acid which comprises at least 40 contiguous nucleotides of SEQ ID NO:1 or SEQ ID NO:3 or the full length complement of SEQ ID NO:1 or SEQ ID NO:3.

11. An isolated nucleic acid of claim 10, which comprises at least 50 contiguous nucleotides of SEQ ID NO:1 or SEQ ID NO:3 or the full length complement of SEQ ID NO:1 or SEQ ID NO:3.

12. An isolated nucleic acid of claim 11, which comprises at least 75 contiguous nucleotides of SEQ ID NO:1 or SEQ ID NO:3 or the full length complement of SEQ ID NO:1 or SEQ ID NO:3.

13. An isolated nucleic acid of claim 12, which comprises at least 100 contiguous nucleotides of SEQ 12D NO:1 or SEQ ID NO:3 or the full length complement of SEQ ID NO:1 or SEQ ID NO:3.

14. An isolated nucleic acid of claim 13, which comprises at least 150 contiguous nucleotides of SEQ ID NO:1 or SEQ ID NO:3 or the full length complement of SEQ I12) NO:1 or SEQ ID NO:3.

15. An isolated nucleic acid of claim 14, which comprises at least 200 contiguous nucleotides of SEQ ID NO:1 or SEQ ID NO:3 or the full length complement of SEQ ID NO:1 or SEQ ID NO:3.

16. An isolated nucleic acid of claim 15, which comprises at least 300 contiguous nucleotides of SEQ ID NO:1 or SEQ ID NO:3 or the full length complement of SEQ ID NO:1 or SEQ ID NO:3.

17. An isolated nucleic acid of claim 16, which comprises at least 400 contiguous nucleotides of SEQ ID NO:1 or SEQ ID NO:3 or the full length complement of SEQ ID NO:1 or SEQ ID NO:3.

18. An isolated nucleic acid of claim 17, which comprises at least 500 contiguous nucleotides of SEQ ID NO:1 or SEQ ID NO:3 or the full length complement of SEQ ID NO:1 or SEQ ID NO:3.

19. An isolated nucleic acid of claim 18, which comprises at least 600 contiguous nucleotides of SEQ ID NO:1 or SEQ ID NO:3 or the full length complement of SEQ ID NO:1 or SEQ ID NO:3.

20. An isolated nucleic acid of claim 19, which comprises at least 616 contiguous nucleotides of SEQ ID NO:1 or SEQ ID NO:3 or the full length complement of SEQ ID NO:1 or SEQ ID NO:3.

21. An isolated nucleic acid of claim 20, which comprises at least 688 contiguous nucleotides of SEQ ID NO:1 or its full length complement.

* * * * *

UNITED STATES PATENT AND TRADEMARK OFFICE
CERTIFICATE OF CORRECTION

PATENT NO. : 5,679,551
DATED : October 21, 1997
INVENTOR(S) : John F. Alderete

It is certified that error appears in the above-identified patent and that said Letters Patent is hereby corrected as shown below:

On the title page, column 2, delete "Assistant Examiner-Wem Yucel" and insert -- Assistant Examiner-Irem Yucel-- therefor.

In claim 2, column 35, line 61, after 'said', insert --nucleic acid-- therefor.

In claim 13, column 37, line 20, delete "SEQ 12D", and insert "SEQ ID-- therefor.

In claim 13, column 37, line 25, delete "SEQ I12)", and insert --SEQ ID-- therefor.

Signed and Sealed this

Twenty-third Day of December, 1997

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 688 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 37..264

( x i ) SEQUENCE DESCRIPTION: SEQ ID NO:1:

```
CAGAGATATC GGTGCAAAAC CTGTACTGTT CCGCTC ATG TCA AGA TTG TGC TCG           54
                                         Met Ser Arg Leu Cys Ser
                                          1               5

GGC GCT ACC CGT TAC CAA TCA GAC ATG TGG TTT ATT TCA CCT ACC CCA          102
Gly Ala Thr Arg Tyr Gln Ser Asp Met Trp Phe Ile Ser Pro Thr Pro
             10              15                  20

CGG CAA GGC AGG ACA CAG AGT ACC CCT GAG ACG CAC AGA CAT ATG CAT          150
Arg Gln Gly Arg Thr Gln Ser Thr Pro Glu Thr His Arg His Met His
         25                  30                  35

TAT CCC TAC TAT CTG CGA CAC TTA CTC TTC GTC ACC CAC AAT GAC GTC          198
Tyr Pro Tyr Tyr Leu Arg His Leu Leu Phe Val Thr His Asn Asp Val
         40              45                  50

TAC AAA ATG CTC AAT GTA AGA CCA ACA ACC AAG AGC CAG CTT ACG CCC          246
Tyr Lys Met Leu Asn Val Arg Pro Thr Thr Lys Ser Gln Leu Thr Pro
 55              60                  65                  70

GCC CAT TAT ACT TGC TTT TAAAGCGGGA GTTATGATTG GCGGGATAAA                 294
Ala His Tyr Thr Cys Phe
                 75

GAACATAAGT AGCAAAAGAG TAAACATCGC CATGAATAGT ACGGCTCAAC ACCTAGGACA        354

ACGTTAAGTC TAAGTAAAGC AGGTGGGTGG TTGACGAGAC ATCCAGTACC TAGAACTCAA        414

CCAGATGCCT CCCCCCTGTA TTACTTCACT ATTCAAAAGC AGGTATAGCA TTCCCATACC        474

ACAGACTGCT CGATGTGAGT CGACCAGAGA GGGCGCTGTA CGAACCTGAA CTATAGACGC        534

GCTCCAGCAT AGGCTGGCCA AAAAAGGCTC ATTCTTCCTC ACAGAAGAAT GCATTACCGC        594

CTATCCCGGG GCTACGTCAG ATAGTTGGTG CCGGGACACT CGTATATGGT TTACACCGAT        654

ATACACTTAA AGACTTCCTA TCGCTTCTTT AAGC                                   688
```

( 2 ) INFORMATION FOR SEQ ID NO:2:

( i ) SEQUENCE CHARACTERISTICS:
        ( A ) LENGTH: 76 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Arg Leu Cys Ser Gly Ala Thr Arg Tyr Gln Ser Asp Met Trp
 1               5                  10                  15

Phe Ile Ser Pro Thr Pro Arg Gln Gly Arg Thr Gln Ser Thr Pro Glu
                 20                  25                  30

Thr His Arg His Met His Tyr Pro Tyr Tyr Leu Arg His Leu Leu Phe
             35                  40                  45
```

```
Val Thr His Asn Asp Val Tyr Lys Met Leu Asn Val Arg Pro Thr Thr
    50                  55                  60

Lys Ser Gln Leu Thr Pro Ala His Tyr Thr Cys Phe
65                  70                  75
```

( 2 ) INFORMATION FOR SEQ ID NO:3:

( i ) SEQUENCE CHARACTERISTICS:
        ( A ) LENGTH: 616 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CGTGTTCAGG GACGTTGCCA CAAGCACGGG TCGTACCTCC CATCCTTAGC GGTTTTGACC    60
AACTACAAGG ACACGCATCC GAGACAGAGC TCCTGCGTCC AGGTATTAGC CCGCTATCTA   120
ACACGCTAGC GTTTTAGAGA CTGACGTCAA TAGCCTTTAC CTACGCAAAC AGAGCCCCT    180
CTTCAACATG CCCACATTGA TCTCAACGAG CCGGGGTACC GACATGGGAC TTCACTCTCA   240
CCGCGTCATT ACGACCTGTA GGTACCTATT ACAGTAACGT CTGGGTCTAG CACTCGGTTT   300
GAACCAAGAT TCGCTATGGG TCGGCAGTCG ACTCGGGGTG AGCAGTCCCG AGGCCCCTT    360
TTGCGCAACG CTGTCCGTAG TTTCGTGATA CAGGCGATGT ACTGTGCCCC TAACCCCGT    420
CCGCCCCATT GCGCCGAACC TCGGTAGCTT TCGACTCTGT ACCCTAATAC TACGACACAT   480
ACCCAGAAAG CGATTTCACC TCATTCTTCC GCAGTAGAGA GATTCCATTG GATGTAGGTG   540
CCCATACATT ACGTATGAGA ATACTACCGG ATACGCGACG CCCGGTAGGC CTAAAAATCA   600
TTTCAGGTTT TTAAGC                                                   616
```

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 4
        ( D ) OTHER INFORMATION: /note= "Y = C or T/U"

( i x ) FEATURE:
        ( A ) NAME/KEY: modified_base
        ( B ) LOCATION: 6
        ( D ) OTHER INFORMATION: /note= "W = A or T/U"

( i x ) FEATURE:
        ( A ) NAME/KEY: modified_base
        ( B ) LOCATION: 7
        ( D ) OTHER INFORMATION: /note= "Y = C or T/U"

( x i ) SEQUENCE DESCRIPTION: SEQ ID NO:4:

```
TCAYTWYTCA TTA                                                       13
```

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
TTTTTGATTA AAG                                                       13
```

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TTTTTTTGA TTAAAG                                                                                                                          16

( 2 ) INFORMATION FOR SEQ ID NO:7:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTTTCAGATT AAAG                                                                                                                           14

( 2 ) INFORMATION FOR SEQ ID NO:8:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTTCAGATTA AAG                                                                                                                            13

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTTTCAGTTT CAGATTAG                                                                                              18

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TACTTCACTT CTCTTAGCGA                                                                                   20

( 2 ) INFORMATION FOR SEQ ID NO:11:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TTGATCACTT CACATTACA                                                                                  19

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TTGTTCACTT CACATTA                                     17

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AGTGTCACTC TTCATCA                                     17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CATCTCATTT TTTAATA                                     17

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CAGACCATTA ATCATTAGTG                                 20

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AATATCATTA TTCAC                                       15

( 2 ) INFORMATION FOR SEQ ID NO:17:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CTCATTCTTC C                                           11

( 2 ) INFORMATION FOR SEQ ID NO:18:

-continued ( i ) SEQUENCE CHARACTERISTICS:
    ( A ) LENGTH: 686 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:18:

| | | | | | | |
|---|---|---|---|---|---|---|
| GCTTAAAAAG | CGATAGGAAG | TCTTTAAGTG | TATATCGGTG | TAAACCATAT | ACGAGTGTCC | 60 |
| CGGCACCAAC | TATCTGACGT | AGCCCCGGGA | TAGGCGGTAA | TGCATTCTTC | TGTGAGGAAG | 120 |
| AATGAGCCTT | TTTTGGCCAG | CCTATGCTGG | AGCGCGTCTA | TAGTTCAGGT | TCGTACAGCG | 180 |
| CCCTCTCTGG | TCGACTCACA | TCGAGCAGTC | TGTGGTATGG | GAATGCTATA | CCTGCTTTTG | 240 |
| AATAGTGAAG | TAATACAGGG | GGGAGGCATC | TGGTTGAGTT | CTAGGTACTG | GATGTCTCGT | 300 |
| CAACCACCCA | CCTGCTTTAC | TTAGACTTAA | CGTTGTCCTA | GGTGTTGAGC | CGTACTATTC | 360 |
| ATGGCGATGT | TTACTCTTTT | GCTACTTATG | TTCTTTATCC | CGCCAATCAT | AACTCCCGCT | 420 |
| TTAAAAGCAA | GTATAATGGG | CGGGCGTAAG | CTGGCTCTTG | GTTGTTGGTC | TTACATTGAG | 480 |
| CATTTTGTAG | ACGTCATTGT | GGGTGACGAA | GAGTAAGTGT | CGCAGATAGT | AGGGATAATG | 540 |
| CATATGTCTG | TGCGTCTCAG | GGGTACTCTG | TGTCCTGCCT | TGCCGTGGGG | TAGGTGAAAT | 600 |
| AAACCACATG | TCTGATTGGT | AACGGGTAGC | GCCCGAGCAC | AATCTTGACA | TGAGCGGAAC | 660 |
| AGTACAGGTT | TTGCACCGAT | ATGTGT | | | | 686 |

( 2 ) INFORMATION FOR SEQ ID NO:19:

( i ) SEQUENCE CHARACTERISTICS:
        ( A ) LENGTH: 628 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

| | | | | | | |
|---|---|---|---|---|---|---|
| GCTTAAAAAC | CTGAAATGAT | TTTTAGGCCT | ACCGGGCGTC | GCGTATCCGG | TAGTATTCTC | 60 |
| ATACAGTAAT | GTATGGGCAC | CTACATCCAA | TGGAATCTCT | CTACTGCGGA | AGAATGAGGT | 120 |
| GAAATCGCTT | TCTGGGTATG | TGCGTAGTAT | TAGGGTACAG | AGTCGAAAGC | TACCGAGGTT | 180 |
| CGGCGCAATG | GGGCGACGGG | GGTTAGGGGC | ACAGTACATC | GCCTGTATCA | CGAAACTACG | 240 |
| GACAGCGTTG | CGCAAAAGGG | GGCCTCGGGA | CTGCTCACCC | CGAGTCGACT | GCCGACCCAT | 300 |
| AGCGAATCTT | GGTTCAAACC | GAGTGCTAGA | CCCAGACGTT | ACTGTAATAG | GTACCTACAG | 360 |
| GTCGTAATGA | CGCGGTGAGA | GTGAAGTCCC | ATGTCGGTAC | CCCGGCTCGT | TGAGATCAAT | 420 |
| GTGGGCATGT | TGAAGAGGGG | GCTCTGTTTG | CGTAGGTAAA | GGCTATTGAC | GTCAGTCTCT | 480 |
| AAAACGCTAG | CGTGTTAGAT | AGCGGGCTAA | TACCTGGACG | CAGGAGCTCT | GTCTCGGATG | 540 |
| CGTGTCCTTG | TAGTTGGTCA | AAACCGCTAA | GGATGGGAGG | TACGACCCGT | GCTTGTGGCA | 600 |
| ACGTCCCTGA | ACACTGAAAA | GGGGATCC | | | | 628 |